US00RE36699E

United States Patent [19]

Murayama

[11] E Patent Number: Re. 36,699

[45] **Reissued Date of Patent: *May 16, 2000**

[54] SONIC DENTAL DEVICE

[76] Inventor: Ronald K. Murayama, 29582 Alta Terra P.O. Box 6599, Laguna Niguel, Calif. 92677

[ * ] Notice: This patent is subject to a terminal disclaimer.

[21] Appl. No.: 09/139,545

[22] Filed: Aug. 25, 1998

Related U.S. Patent Documents

Reissue of:

[64] Patent No.: 5,636,988
Issued: Jun. 10, 1997
Appl. No.: 08/334,586
Filed: Nov. 4, 1994

[63] Continuation-in-part of application No. 08/300,414, Sep. 2, 1994, abandoned, which is a continuation-in-part of application No. 07/998,378, Dec. 30, 1992, Pat. No. 5,343,883.

[51] Int. Cl.[7] ..... A61C 17/20

[52] U.S. Cl. ..... 433/118; 433/119

[58] Field of Search ..... 433/118, 119; 132/322; 601/2

[56] References Cited

U.S. PATENT DOCUMENTS

| | | | |
|---|---|---|---|
| Re. 35,712 | 1/1998 | Murayama | 132/322 |
| 3,183,538 | 5/1965 | Hubner | 15/22.1 |
| 3,421,524 | 1/1969 | Waters | 132/322 |
| 3,466,689 | 9/1969 | Aurelio et al. | 128/66 |
| 3,809,977 | 5/1974 | Balamuth et al. | 433/119 |
| 3,847,167 | 11/1974 | Brien | 132/322 |
| 4,014,354 | 3/1977 | Garrett | 132/90 |
| 4,127,125 | 11/1978 | Takemoto et al. | 433/119 |
| 4,162,576 | 7/1979 | Takemoto et al. | 128/229 |
| 4,235,253 | 11/1980 | Moore | 132/92 R |
| 4,245,658 | 1/1981 | Lecouturier | 132/92 R |
| 4,265,257 | 5/1981 | Salyer | 132/92 R |
| 4,307,740 | 12/1981 | Florindez et al. | 132/92 R |
| 4,326,549 | 4/1982 | Hinding | 132/92 R |
| 4,338,957 | 7/1982 | Meibauer | 132/91 |
| 4,458,702 | 7/1984 | Grollimund | 132/92 A |
| 4,490,114 | 12/1984 | Kleesattel et al. | 433/119 |
| 4,586,521 | 5/1986 | Urso | 132/92 R |
| 4,605,025 | 8/1986 | McSpadden | 132/92 R |
| 4,880,382 | 11/1989 | Moret et al. | 433/118 |
| 5,016,660 | 5/1991 | Boggs | 132/322 |
| 5,033,150 | 7/1991 | Gross et al. | 132/322 |
| 5,069,233 | 12/1991 | Ritter | 132/322 |
| 5,085,236 | 2/1992 | Odneal et al. | 132/325 |
| 5,100,321 | 3/1992 | Coss et al. | 433/118 |
| 5,133,661 | 7/1992 | Euvrard | 433/120 |
| 5,170,809 | 12/1992 | Imai et al. | 132/322 |
| 5,343,883 | 9/1994 | Murayama | 433/118 |

OTHER PUBLICATIONS

Power Floss Brush brochure by Panasonic.

*Primary Examiner*—Edgar Burr
*Assistant Examiner*—Daniel J. Colilla
*Attorney, Agent, or Firm*—Lyon & Lyon LLP

[57] ABSTRACT

An electric device which removes supragingival and subgingival plaque and undesirable debris from the interproximal surfaces between teeth is described. This device utilizes a combination of sonic energy and dental floss which is secured between two tines, the tines being part of a flexible fork which is removable from a powered handle which contains batteries and an electric motor. The electric motor, which is coupled to an eccentrically mounted disc on an output shaft, revolves at sonic frequencies which in turn generates sonic energy that is transmitted to the flexible fork which holds the floss. The sonic energy is synchronized and in tune with the natural resonance frequencies of the fork thereby stimulating the resonance action of oscillating vertical and/or elliptical movement of the fork which in turn imparts cleaning energy to and enhances the cleaning properties of the floss. The flexible fork may be removed from the handle and replaced with other dental cleaning tools such as a brush, a pick, and/or a tray attachment.

31 Claims, 6 Drawing Sheets

32
31
31
10
12

28
16

18
14
20
22
24
30
26

31
12
10
28
16
18
14
20
22
24
26
30

20
18
28
20
16

SONIC DENTAL DEVICE

Matter enclosed in heavy brackets [ ] appears in the original patent but forms no part of this reissue specification; matter printed in italics indicates the additions made by reissue.

This is a continuation-in-part of U.S. application Ser. No. 08/300,414, filed on Sep. 2, 1994, now abandoned, which is a continuation-in-part of U.S. application Ser. No. 07/998, 378, filed on Dec. 30, 1992, now U.S. Pat. No. 5,343,883.

FIELD OF INVENTION

The present invention relates to personal hygiene, particularly dental hygiene including flossing, cleaning, disinfecting, and/or bleaching teeth.

BACKGROUND

Presently, a majority of dental disease occurs on interproximal surface areas of teeth (i.e. the surface areas between teeth). A program of good dental hygiene which includes keeping the interproximal surface areas clean helps prevent dental disease from occurring in these areas.

Flossing is a well known and commonly used method of good dental hygiene by which interproximal surfaces of teeth are cleaned. Proper flossing cleans the interproximal surfaces both above and below the gum line thereby reducing the likelihood of dental disease on these surfaces. Although flossing is a valuable part of good dental hygiene, it is a tedious and time consuming task and, therefore, is seldom done properly. Cleaning the interproximal areas of teeth has been a problem since the existence of teeth.

There are various methods of cleaning teeth. Each method has limitations with regard to cleaning the interproximal surfaces of teeth. Toothbrushes are used to clean teeth. However, toothbrushes cannot adequately clean interproximal surface areas because of the lack of access to these areas. Toothpicks are also used to clean teeth and also suffer from an inability to reach all interproximal surfaces adequately. Hydraulic dental irrigation systems may be used to clean these areas. However, it is well accepted that hydraulic irrigation alone is inadequate to remove the sticky plaque films which build up on teeth surfaces including interproximal surfaces.

The best method of cleaning the interproximal surfaces of teeth is to have a dental cleaning done by a health professional. However, dental flossing is generally regarded as the next best and the most convenient way a lay person can properly clean between his or her own teeth.

If done properly, dental flossing is a highly effective method of improving dental hygiene and health of both teeth and periodontium (gum tissues and underlying jaw bone) which is between natural teeth and/or dental restorations in the mouth. Flossing action actually mechanically cleans bacteria laden plaque from tooth surfaces, particularly from interproximal tooth surfaces. Essentially, the floss wipes or scrubs off plaque and other undesirable debris from tooth surfaces. Although flossing is commonly known to be as important and as necessary as tooth brushing, it is widely neglected. Some of the most common complaints about flossing (and, therefore, reasons for neglect) include that it is difficult to perform and is time consuming.

A variety of devices have been introduced which attempt to make flossing easier. Most of these devices simply act as holders for the floss to reduce the manual dexterity required to floss. While such floss-holder devices may simplify some aspects of flossing, they generally have a fixed or limited range of motion and, therefore, have limited cleaning action and effectiveness. In addition, floss-holder devices are used manually, the cleaning energy conveyed to plaque covered tooth surfaces must be supplied by the user.

Electrically powered devices for flossing and cleaning teeth have also been introduced. Most of these devices directly connect floss or floss-holding assemblies to a power source such as an electric motor. Because of the direct connection between the motor and the flossing element, whether it is by drive shafts, gears, pulleys, cams, or etc., these devices impart gross movement of the floss between the teeth which is forceful, jerky, and/or "sawing" or "hatchet-like" in nature. These types of movement can be both inefficient and potentially harmful.

Generally, these electrically powered devices comprise flossing assemblies attached to well known electric toothbrush handles. Thus, many electric flossers utilize the up and down or back and forth movement of an electric toothbrush assembly. Many devices have been described which reciprocate a strand of floss back and forth between teeth thereby resulting in a sawing motion. See,. e.g., Brien, U.S. Pat. No. 3,847,167; Lecouturier, U.S. Pat. No. 4,245,658; Salyer, U.S. Pat. No. 4,265,257; Hinding, U.S. Pat. No. 4,326,549; Meibauer, U.S. Pat No. 4,338,957; Boggs, U.S. Pat. No. 5,016,660; and Gross, et al., U.S. Pat. No. 5,033,150. Some devices have been described which move a strand of floss in an up and down or hatchet-like motion between teeth. See, e.g., Garrett, U.S. Pat. No. 4,014,354; Moore, U.S. Pat. No. 4,235,253; Grollimund, U.S. Pat. No. 4,458,702; and McSpadden, U.S. Pat. No. 4,605,025. Additional devices have been described which combine both a back and forth motion and an up and down motion. See, e.g., Florindez et al., U.S. Pat. No. 4,307,740; Urso, U.S. Pat. No. 4,586,521; and Ritter, U.S. Pat. No. 5,069,233. Still other devices have been described which incorporate an approximate teeter-totter or see-saw action whereby floss reciprocates over an imaginary fulcrum which lies along the long axis of the device. See, e.g., Waters, U.S. Pat. No. 3,421,524; and Odneal et al., U.S. Pat. No. 5,085,236.

One problem with some of these devices is that they utilize a mere back and forth or horizontal manipulation of dental floss between teeth. It is well accepted in the dental community that mere back and forth manipulation of dental floss between teeth is ineffective in cleaning teeth surfaces. Therefore, devices which merely provide a back and forth sawing motion are ineffective for flossing purposes.

Another problem with these devices is that they use direct mechanical links to transfer energy from an electric motor to a flossing assembly. Due to the direct mechanical links, the flossing assemblies are not "forgiving" (i.e. they meet resistance with force). If when using one of these devices the flossing element comes in contact with soft mouth tissues, the tissues may very well be cut or abraded. In addition, if floss is moved between teeth in a rapid and/or strong back and forth motion, it can injure and damage mouth tissues. Furthermore, it is also well recognized that sharp or rapid up and down hatchet motions are more effective for flossing purposes, but are also potentially damaging to periodontal tissues.

Some devices include features to specifically address the potential injury problem See, e.g., Meibauer, U.S. Pat. No. 4,338,957; and Grollimund, U.S. Pat. No. 4,458,702. However, the problems persist due to the direct mechanical links between the motor and the flossing assembly.

Energy, such as vibrational energy in sonic frequency ranges (e.g. 2,000 to 20,000 cycles per minute (cpm)), may be indirectly linked between a motor and a tool assembly. A sonic energy dental cleaning device is disclosed in Aurello et al., U.S. Pat. No. 3,466,689. Although the device described does not use direct mechanical links, it merely uses "acoustic streaming" (i.e. liquid under the influence of oscillatory forces) to clean teeth. This patent describes that teeth are not directly physically scrubbed or rubbed, rather the cleaning is accomplished completely by indirect acoustic streaming. However, as noted above, it is well accepted that hydraulic irrigation alone is not adequate to remove the sticky plaque films which build up on teeth surfaces including interproximal surfaces. There remains a need for a device which physically contacts teeth to clean them, but which does not utilize direct mechanical links.

SUMMARY OF THE INVENTION

Unlike the devices cited above, the present invention uses sonic energy which is synchronized with natural resonance frequencies of a flexible "fork" which holds a strand of dental floss between a pair of "tines." The present invention bypasses mechanical complexities and limitations due to direct mechanical links to an electric motor. By using sonic energy instead of mechanical energy, energy can be transmitted from the power source to the floss in an effective and efficient manner due to a minimum number of moving parts which consequently reduces friction and energy loss. The use of sonic energy imparted to the floss is gentle and forgiving to soft gingival tissues while still making available a very potent and effective form of direct cleaning energy.

The present invention includes an eccentric counterweight placed on an output shaft of an electric motor which rotates and produces sonic energy (i.e. vibrational energy in the sonic range). The motor operates at optimal ranges of sonic frequencies (between 2,000 and 20,000 cpm but ideally between 8,000 and 17,000 cpm) which correspond to the natural resonance frequencies of the flexible floss-holding fork.

As dictated by physical properties and molecular composition, virtually every type of solid matter has an inherent resonance frequency which allows the material to move and/or vibrate in a certain fashion when exposed to certain types of oscillating energy such as sonic energy. The electric motor operates in tune with the natural resonance frequency of the floss-holding fork part of the device. Sonic energy generated by the electric motor is imparted to the handle and, thus, to the floss-holding fork which is attached to the handle. The sonic energy stimulates the inherent resonance frequency of the floss-holding fork which causes the fork to move in one or both of two different patterns of movement: (1) small elliptical movements around the long axis of the device; and/or (2) reciprocating movement in the plane perpendicular to the long axis of the device (up and down along the long axis of the tooth). These patterns of cleaning movement can occur under a working load such as when the device is actually being used in a mouth. The resonance action or movement of the floss-holding fork is similar in principle to how a musical tuning fork works. Hence the resonance action stimulated by sonic energy is frequency sensitive. The resonance action can be better viewed with the aid of a strobe light.

In essence, the electric motor imparts sonic energy at optimal resonance frequencies to the handle of the device. The floss-holding fork is attached to the handle and receives the sonic energy from the handle at a frequency which stimulates resonance action in the fork consequently moving the fork and the floss which it is holding. Thus, the resonance action of the floss-holding fork ultimately transfers sonic energy to the floss such that tooth surfaces may be cleaned. The resonance action is of considerable value and effectiveness with respect to enhancing the cleaning abilities of this flossing device.

It is an object of the present invention to provide a device which stimulates movement of a strand of floss through sonic energy and resonance action such that the floss may be placed between teeth and movement of the floss may clean between those teeth.

It is an additional object of the present invention to provide a device which uses sonic energy and resonance action to stimulate and move a strand of dental floss in a manner which operates under load and which is forgiving in that it will not injure mouth tissues.

It is also an object of the present invention to provide a device which stimulates gum tissue via massaging the gums by being in contact with the vibrating floss.

It is an additional object of the present invention to provide a device which uses sonic energy and resonance action to move a floss-holding assembly and which floss-holding assembly may be replaced with a toothbrush assembly which is similarly stimulated such that rapid small circular movements and/or gentle reciprocating "up and down" movements of the brush bristles occur.

It is a further object of the present invention to provide a device which uses sonic energy and resonance action to move a pick attachment in a manner similar to that described above for the flosser and toothbrush.

It is yet another object of the present invention to use sonic energy to improve the ease of passing floss through tight contact areas between teeth.

It is yet a further object of the present invention to provide a device which uses sonic energy and resonance action to move a dental mouth tray attachment in a manner similar to that described above for the flosser, toothbrush, and pick.

It is still a further object of the present invention to provide a device which uses sonic energy and resonance action to move a floss-holding assembly and which floss-holding assembly may be replaced with a mouth tray assembly which may be stimulated by the sonic energy such that materials held by the mouth tray assembly are similarly stimulated.

It is still an additional object of the present invention to increase the ease and effectiveness of mechanical flossing and teeth cleaning by a lay person.

DETAILED DESCRIPTION OF THE PREFERRED EMBODIMENT

Figures 1A, 1B, 1C, 1D:
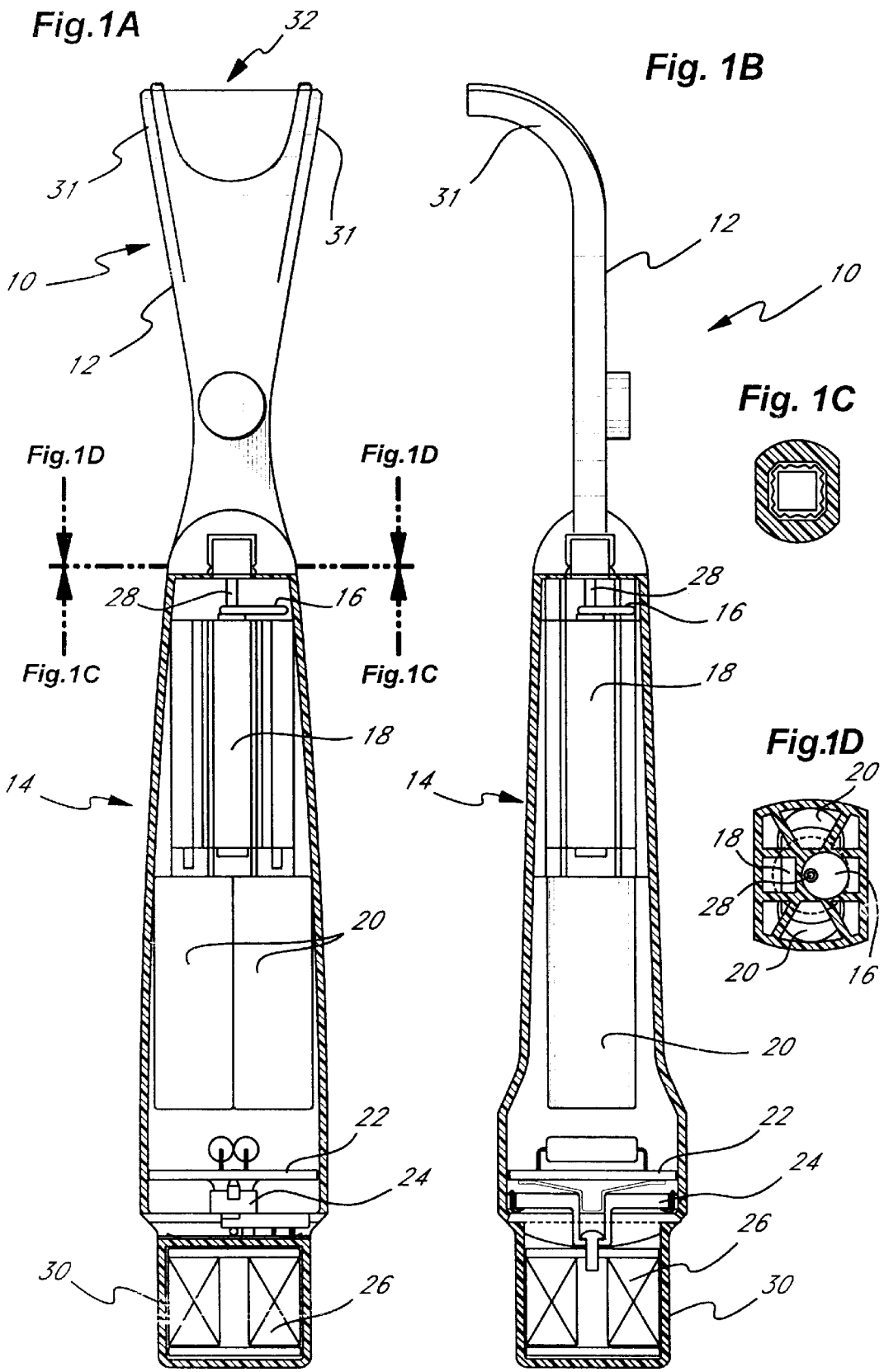
FIG. 1A is a front plan view of the present invention showing certain features in phantom.
FIG. 1B is a side plan view of the present invention showing certain features in phantom.
FIG. 1C is a cross-sectional view taken along line 1C—1C in FIG. 1A.
FIG. 1D is a cross-sectional view taken along line 1D—1D in FIG. 1A.
Figure 2A:
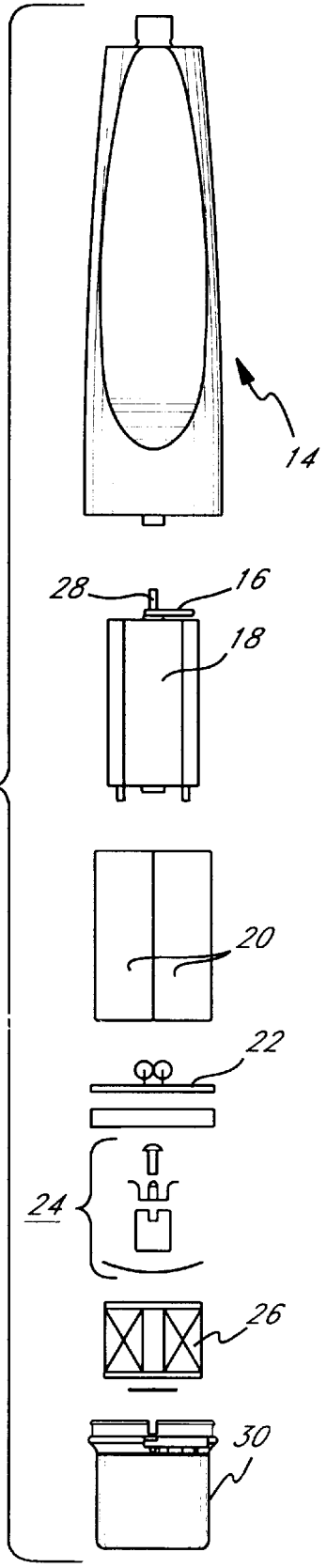
FIG. 2A is a front exploded view of the power driven handle of the present invention.
Figure 2B:
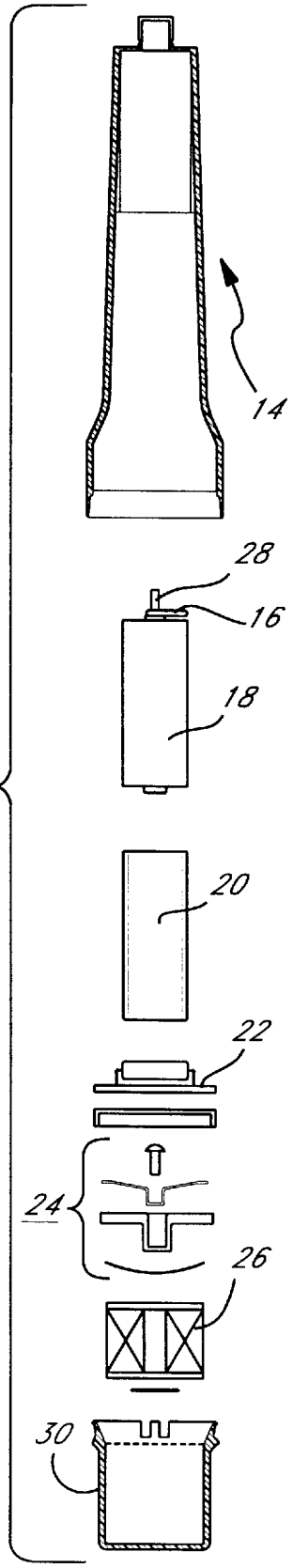
FIG. 2B is a side exploded view of the power driven handle of the present invention.

A sonic dental cleaning device 10 is described herein and shown in the Figures. The device 10, when assembled as a flossing device (FIGS. 1A and 1B), comprises two main pieces: (1) a hollow power driven handle 14 having two ends (also see FIGS. 2A and 2B); and (2) a detachable floss-holding fork 12 wherein one end of the fork 12 attaches to the handle 14 at one end and another end of the fork 12 forming a pair of tines 31 which hold floss 32. The handle 14 is preferably made of polymeric plastic and the fork 12 and tines 31 are preferably made of nylon or polymeric plastics. Located at another end of the handle 14, opposite the end attached to the fork 12, is a handle end piece 30 which holds a charging coil 26 which enables recharging the device 10 by induction in a conventional manner.

As shown in FIGS. 1A, 1B, 2A, and 2B, the handle 14 includes an electric motor 18 located therein which has an output shaft 28 and an eccentrically mounted disc 16 attached thereto. Power for the electric motor 18 is stored in and supplied by batteries 20 which are also located in the handle 14. An electric circuit board 22 and a multi-speed on/off switch assembly 24 are located between the batteries 20 and the recharging coil 26. The circuit board 22 and the multi-speed switch 24 control the flow of electrical current from the batteries 20 to the motor 18 which ultimately determines the speed of the motor 18.

The disc 16 has a specific weight, shape and size and is eccentrically mounted on the output shaft 28 of the motor 18. The motor 18 causes the output shaft 28 and, therefore, the disc 16 to rotate at certain predetermined frequencies which are regulated by the circuit board 22 and switch 24 settings. When the disc 16 rotates at given frequencies, vibrational energy occurs which manifests itself in the form of sonic energy. As the handle 14 absorbs the resultant sonic energy, the sonic energy is consequently transmitted to the floss-holding fork 12 which is attached to the handle 14.

When the floss-holding fork 12 absorbs the proper frequency and intensity of sonic energy the fork 12 will oscillate in a desirable up and down motion and/or small elliptical motion around the long axis of the device 10. The up and down motion is designated with Arrows A in FIG. 3. This phenomenon is called the "resonance action" of the floss-holding fork 12 since it occurs only when the one of the natural resonance frequencies of the fork 12 is in tune with the frequency and intensity of the sonic energy it is exposed to.

The phenomenon of resonance action is related to physical limitations of a vibrating body or medium and hence the resonance action of the floss-holding fork 12 will only occur under very specific scientifically determinable conditions. In order for the resonance action to occur, all elements of the device 10 must be in tune and in harmony with one another. The given material composition, design, size, shape and mass of the floss-holding fork 12 determines its inherent "natural resonance frequency" which is what allows the fork 12 to move in a prescribed manner when exposed to certain forces. This is somewhat analogous to the resonance frequency of a musical tuning fork. A musical tuning fork vibrates only in a specific note or pitch which corresponds to the resonance frequency of the tuning fork.

In order for the floss-holding fork 12 to move or "resonate" properly, all elements of the handle 14 must be balanced with or in tune with the resonance frequency of the fork 12. In other words, the eccentrically mounted disc 16 must be of a specific size, shape, mass, and eccentricity and must rotate at specific frequencies which may be predetermined by the circuit board 22 and switch 24 settings. Also, the overall design, size, shape, and mass of the handle 14 and all of the components therein are critical. All of these elements must be in the proper balance in order for the floss-holding fork 12 to move with the desired resonance action.

The following are examples of dimensions of certain elements of a preferred embodiment of the present invention. The handle 14 is preferably between approximately 130 mm. and 155 mm. in length and approximately 150 g. to 200 g. in weight. The floss-holding fork 12 is preferably between approximately 70 mm. and 80 mm. in length and approximately 5 g. to 12 g. in weight. The distance between the tines 31 is approximately 20 mm. to 30 mm. apart. The eccentric disc 16 is between approximately 8 mm. to 12 mm. in diameter and approximately 0.8 g. to 1.5 g. in weight. As described above, in the preferred embodiment the rotation of the disc 16 is between 2,000 and 20,000 cpm and preferably between 8,000 and 17,000 cpm.

A variety or range of speeds or frequencies of operation are needed because the natural resonance frequency and, consequently, the resonance action, of the floss-holding fork 12 will change according to how much of a "load" is placed on the floss 32 held by the fork 12. There are a variety of sonic frequencies employed in the present invention 10 which are intended to allow the resonance action of the fork 12 to occur under conditions of varying loads (i.e. different amounts of friction and resistance imposed upon the floss 32 during use of the device 10). As the load varies, so win the inherent natural resonance frequency of the fork 12. Thus, having a variety of frequencies is necessary.

The present invention relies upon sonic energy, natural resonance frequencies and the resultant resonance action. This combination utilizes a minimal number of moving parts thereby reducing friction and using cleaning energy more efficiently.

Figure 3A:
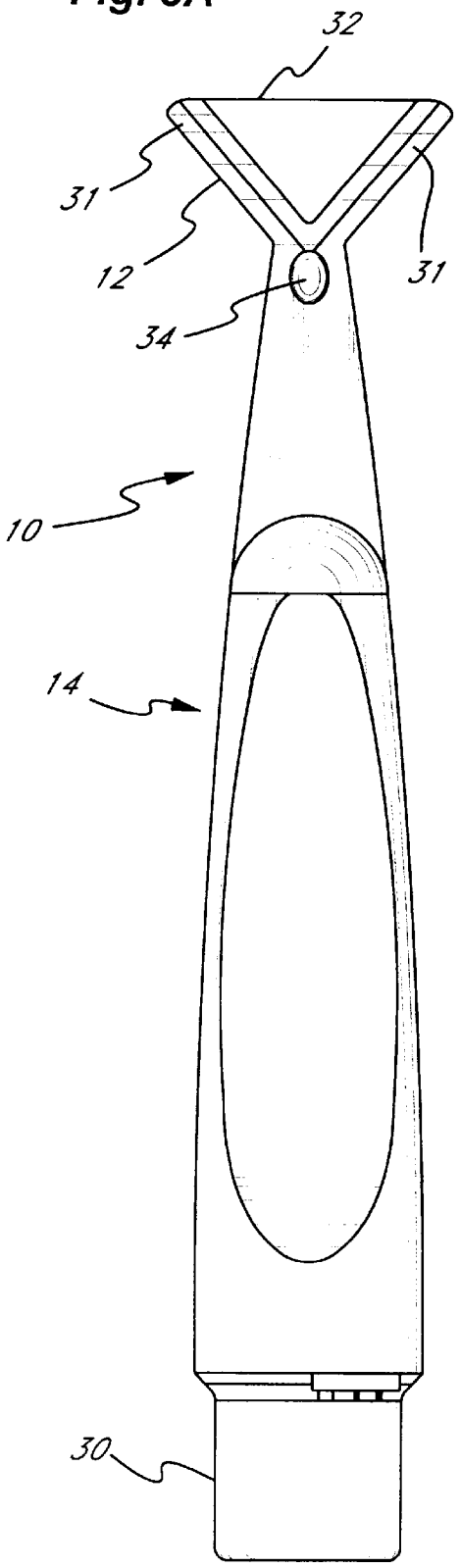
FIG. 3A is a front plan view of a preferred embodiment of the present invention with a floss attachment.
Figure 3B:
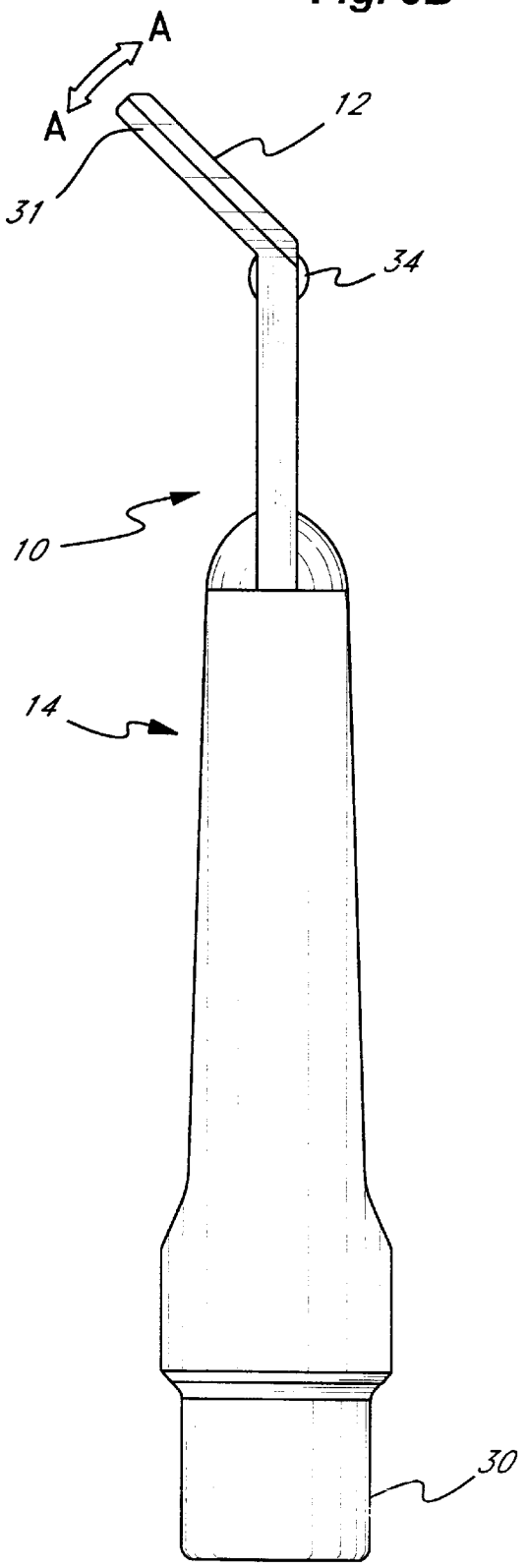
FIG. 3B is a side plan view of a preferred embodiment of the present invention with a floss attachment.

FIGS. 3A and 3B illustrate a second embodiment of a floss-holding fork 12. Although different, the overall design of the second embodiment fork 12 enables operation of the device 10 by the same working principles of coupling sonic energy with the natural resonance frequencies of the fork 12 as described above. Also shown in FIGS. 3A and 3B is a locking cap 34 which secures the floss 32 to the fork 12. Arrows A in FIG. 3B illustrate the motion of the floss-holding fork 12.

Figure 4A:
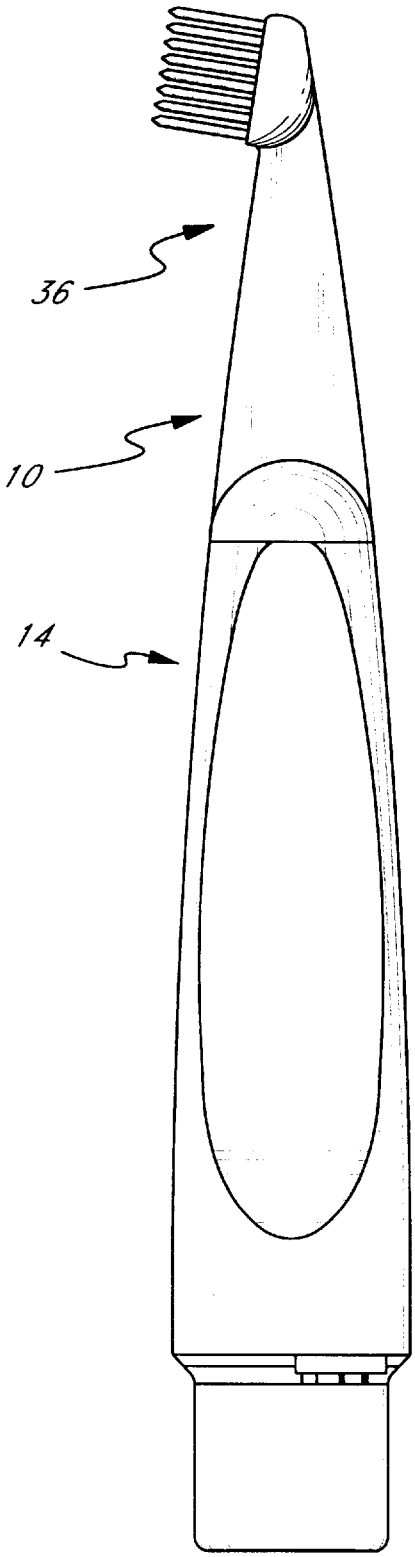
FIG. 4A is a front plan view of the present invention with a toothbrush attachment.
Figure 4B:
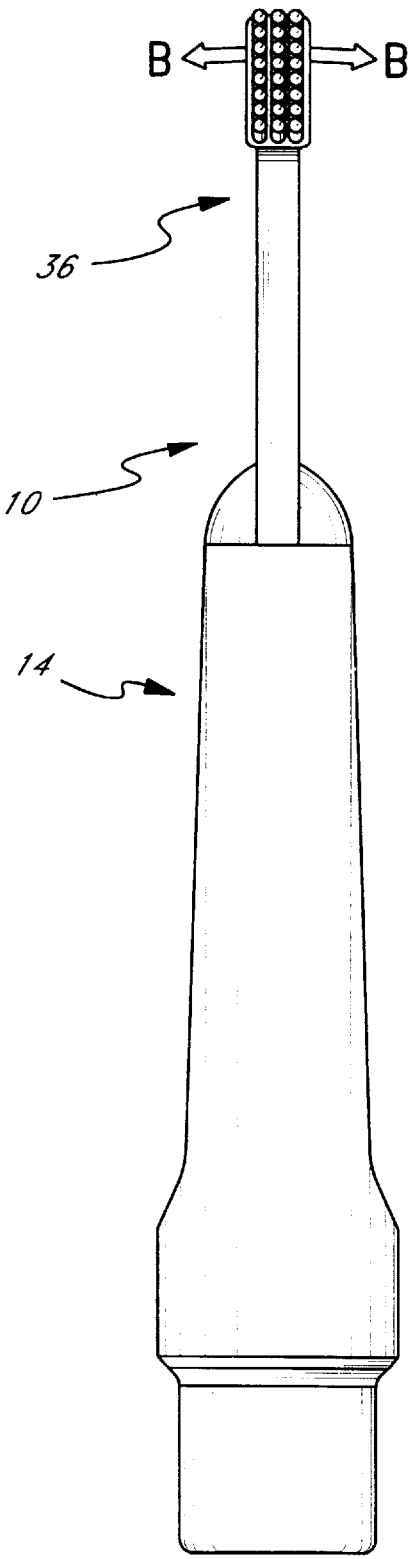
FIG. 4B is a side plan view of the present invention with a toothbrush attachment.

FIGS. 4A and 4B illustrate an embodiment of the present invention 10 which includes a toothbrush attachment 36. The same working principle of coupling sonic energy with the natural resonance frequencies of the toothbrush attachment 36 as described above apply to this embodiment. Arrows B in FIG. 4B illustrate the motion of the toothbrush attachment 36.

Figure 5A:
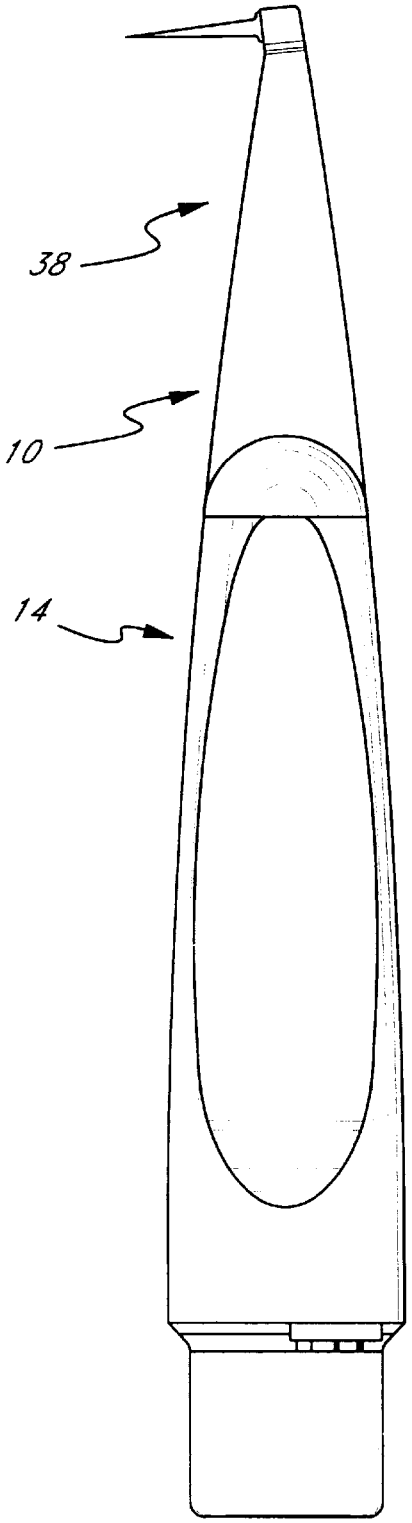
FIG. 5A is a front plan view of the present invention with a pick attachment.
Figure 5B:
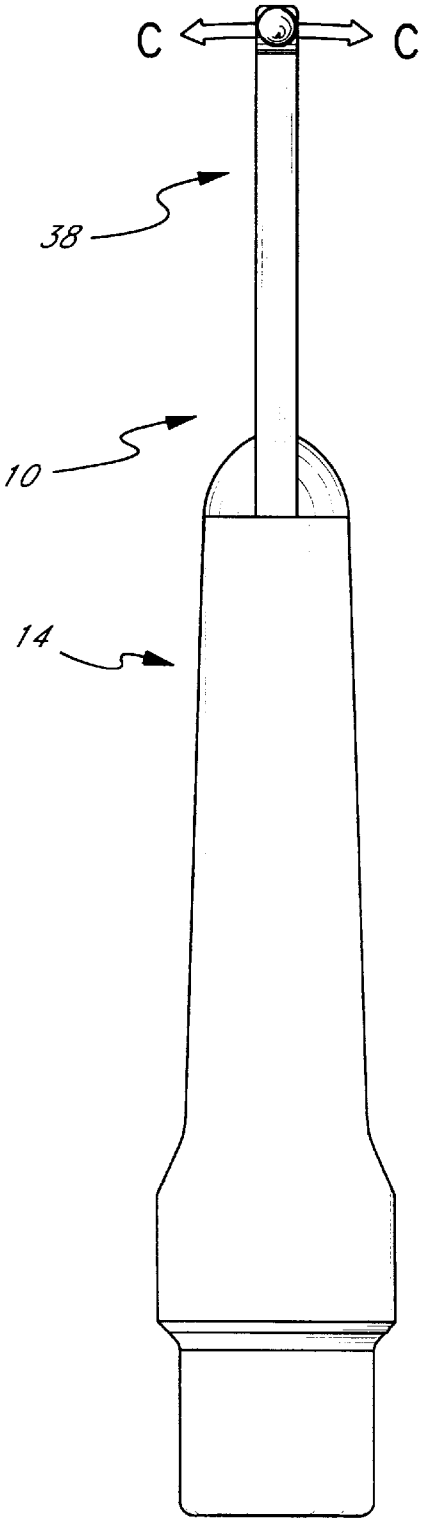
FIG. 5B is a side plan view of the present invention with a pick attachment.

FIGS. 5A and 5B illustrate another embodiment of the present invention 10 which includes a pick attachment 38. The utilization of sonic energy and resonance action to drive the pick attachment 38 as described above also applies to this embodiment. Arrows C in FIG. 5B illustrate the motion of the pick attachment 38.

Figure 6A:
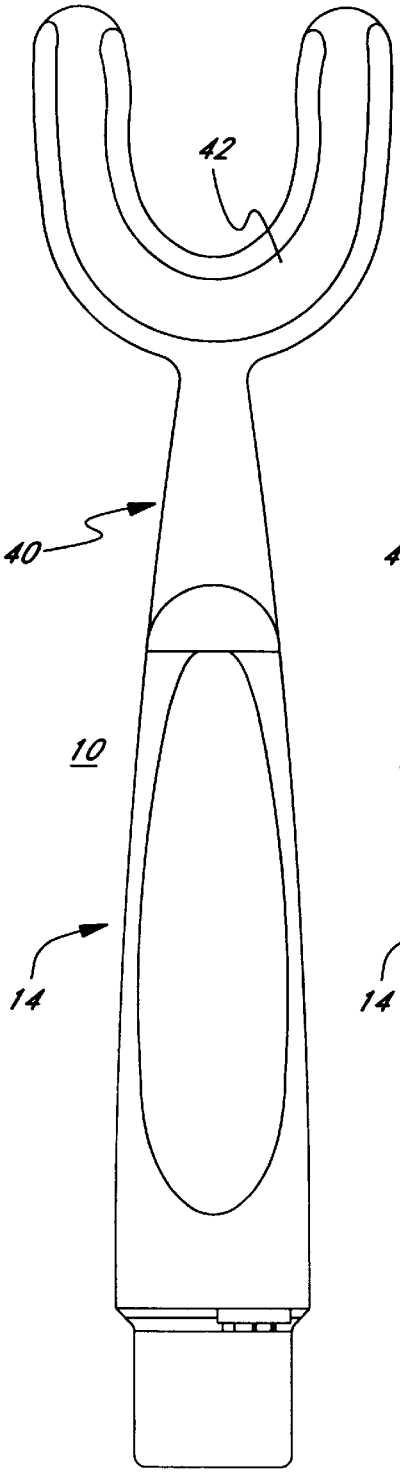
FIG. 6A is a front plan view of the present invention with a dental mouth tray attachment.
Figure 6B:
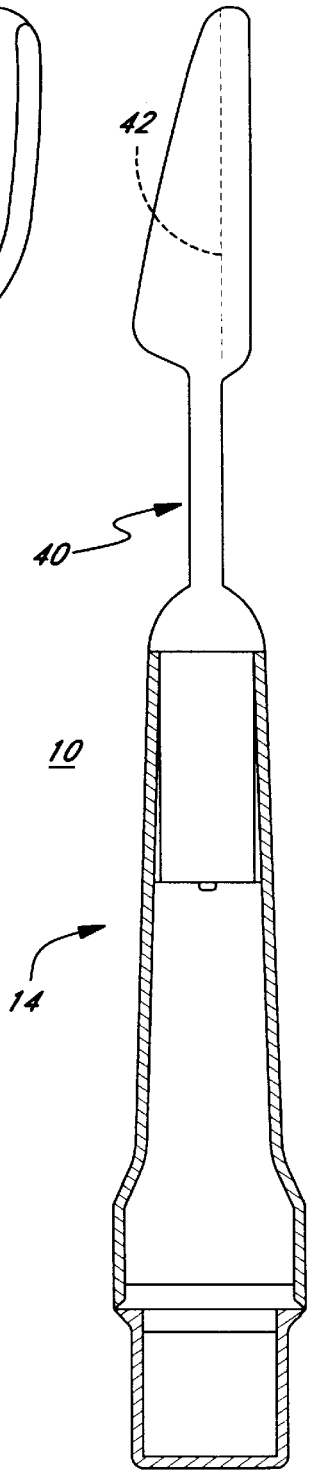
FIG. 6B is a side plan view of the present invention with a single tray dental mouth tray attachment.
Figure 6C:
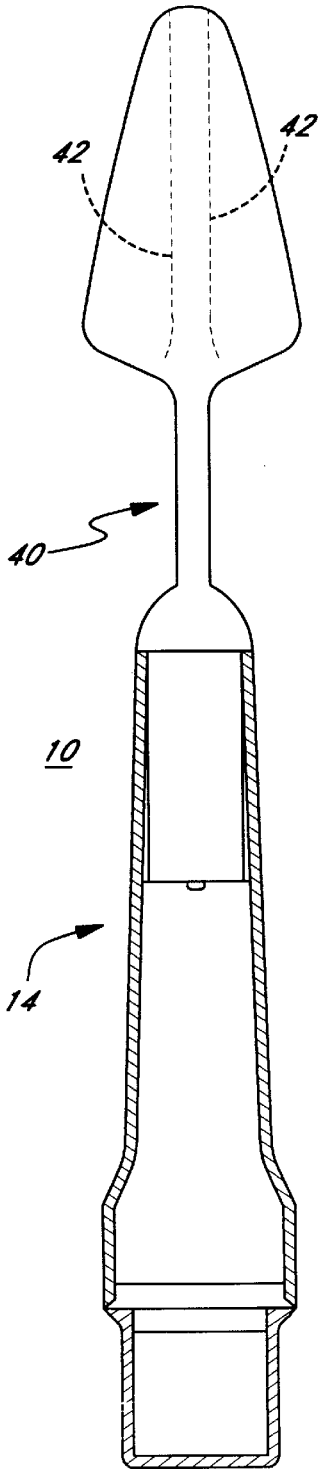
FIG. 6C is a side plan view of the present invention with a double tray dental mouth tray attachment.

FIGS. 6A, 6B, and 6C illustrate an additional embodiment of the present invention 10 which includes a dental mouth tray attachment 40. The dental mouth tray 40 is preferably formed to fit over the teeth of a user. The dental mouth tray attachment 40 may be a single tray designed to fit over either the upper or lower teeth of the user, as is shown in FIGS. 6A and 6B, or a double tray designed to fit over both the upper and lower teeth of the user at the same time, as is shown in FIG. 6C. In both designs, the portion of the tray attachment 40 which fits over the teeth of the user is preferably made from a soft plastic or elastic material. In both designs, the tray attachment 40 provides a trough 42 for holding different materials to which the users teeth are to be exposed. For example, the trough 42 of the tray attachment 40 may hold such materials as cleaning solution, bleaching gels, or other chemicals, mixtures, or compounds. Such materials may be used, for example, to clean, disinfect, and/or bleach teeth.

The tray attachment 40 allows teeth to be exposed to various fluids or gels without filling the entire oral cavity with the fluids or gels. When the tray attachment 40 is coupled to the power handle 14, sonic energy may be transferred from the power handle 14 to the tray attachment 40 via the same principles as are described above. Consequently, the sonic energy may be transferred to the materials held in the trough 42 of the tray attachment 40. The sonic energy stimulates, activates, and/or enhances the effectiveness and action of the materials held in the trough 42 of the tray attachment 40.

While embodiments of the present invention have been shown and described, various modifications may be made without departing from the scope of the present invention, and all such modifications and equivalents are intended to be covered.

I claim:

1. A device for cleaning teeth comprising a handle containing an eccentric counterweight attached to a motor for rotating the counterweight and producing vibrational energy in frequencies between 2,000 and 20,000 cpm, a floss-holding member comprising a pair of tines for holding a strand of floss therebetween, the floss-holding member being detachably attached to the handle for allowing the vibrational energy produced by the counterweight to induce a resonance action in the floss-holding member for moving the strand of floss, and a dental mouth tray member which is attachable to the handle in place of the floss-holding member.

2. The device of claim 1 wherein the frequency of the vibrational energy induces a resonance action in the dental mouth tray member to cause the dental mouth tray member to move.

3. A device for cleaning teeth comprising a handle containing an eccentric counterweight attached to a motor for rotating the counterweight and producing vibrational energy in frequencies between 2,000 and 20,000 cpm, a power supply for energizing the motor, a floss-holding member comprising a pair of tines for holding a strand of floss therebetween, the floss-holding member being detachably attached to the handle for allowing the vibrational energy produced by the motor to be transmitted to the floss-holding member to cause the floss-holding member to move and thereby the strand of floss to move, and a dental mouth tray member which is attachable to the handle in place of the floss-holding member, wherein the frequency of the vibrational energy induces a resonance action in the dental mouth tray member to cause the dental mouth tray member to move.

4. A device for cleaning teeth comprising a handle containing an eccentric counterweight attached to a motor for rotating the counterweight and producing vibrational energy in frequencies between 2,000 and 20,000 cpm, and a floss-holding member comprising a pair of tines for holding a strand of floss therebetween, the floss-holding member being detachably attached to the handle for allowing the vibrational energy produced by the counterweight to induce a resonance action in the floss-holding member for moving the strand of floss.

5. The device of claim 4 further including a different dental cleaning tool which is attachable to the handle in place of the floss-holding member.

6. The device of claim 5 wherein the different dental cleaning tool comprises a toothbrush member.

7. The device of claim 6 wherein the frequency of the vibrational energy induces a resonance action in the toothbrush member to cause the toothbrush member to move.

8. The device of claim 5 wherein the different dental cleaning tool comprises a toothpick member.

9. The device of claim 8 wherein the frequency of the vibrational energy induces a resonance action in the toothpick member to cause the toothpick member to move.

10. A method of cleaning tooth surfaces comprising the steps of (a) removably attaching a floss-holding member to a handle containing an eccentric counterweight attached to a motor for rotating the counterweight, (b) attaching dental floss to the floss-holding member, (c) inserting the dental floss between teeth, (d) inducing movement in the floss-holding member through rotating the eccentric counterweight thereby producing vibrational energy in frequencies between 2,000 and 20,000 cpm for inducing resonance action in the floss-holding member for causing the dental floss to move between the teeth, and (e) attaching a different dental cleaning tool to the handle in place of the floss-holding member.

11. A method of cleaning tooth surfaces comprising the steps of (a) attaching dental floss to a floss-holding member, (b) inserting the dental floss between two teeth, and (c) inducing movement in the floss-holding member through rotating an eccentric counterweight thereby producing vibrational energy in frequencies between 2,000 and 20,000 cpm for inducing resonance action in the floss-holding member which causes the dental floss to move between the two teeth.

12. The method of claim 11 comprising the further steps of (a) removing the floss holding member, (b) attaching a toothbrush member, and (c) inducing movement in the toothbrush member through rotating an eccentric counterweight thereby producing vibrational energy in frequencies between 2,000 and 20,000 cpm for inducing resonance action in the toothbrush member for causing the toothbrush member to move.

13. The method of claim 11 comprising the further steps of (a) removing the floss holding member, (b) attaching a toothpick member, and (c) inducing movement in the toothpick member through rotating an eccentric counterweight thereby producing vibrational energy in frequencies between 2,000 and 20,000 cpm for inducing resonance action in the toothpick member for causing the toothpick member to move.

14. A device for cleaning teeth comprising a handle containing a motor which rotates an eccentric counterweight thereby producing vibrational energy in frequencies between 2,000 and 20,000 cpm, a floss-holding member comprising a pair of tines for holding a strand of floss therebetween, the floss-holding member being attached to the handle to allow the vibrational energy produced by the motor to be transmitted to the floss-holding member to cause the floss-holding member to move and thereby the strand of floss to move, the floss-holding member being detachable from the handle, and a dental mouth tray member is attachable to the handle in place of the floss-holding member, wherein the frequency of the vibrational energy induces a resonance action in the dental mouth tray member to cause the dental mouth tray member to move.

*15. A device for cleaning teeth comprising*

*a handle containing an eccentric counterweight attached to a motor for rotating the counterweight and producing vibrational energy in frequencies between 8,000 and 20,000 cpm; and*

*a dental cleaning member detachably attached to the handle, the dental cleaning member having a material composition, size, shape and mass defining a natural resonance frequency in resonance with the frequencies in the sonic range for allowing the vibrational energy produced by the counterweight to induce a resonance action in the dental cleaning member for moving the dental cleaning member in a reciprocating movement in a plane.*

*16. The device of claim 15, wherein said dental cleaning member comprises a toothbrush member.*

*17. The device of claim 15, wherein said dental cleaning member comprises a dental mouth tray member.*

*18. The device of claim 15, wherein said dental cleaning member comprises a toothpick member.*

*19. The device of claim 15, wherein the dental cleaning member comprises a floss-holding member.*

*20. A device for cleaning teeth comprising*

*a handle containing an eccentric counterweight attached to a motor for rotating the counterweight and producing vibrational energy in frequencies between 8,000 and 20,000 cpm; and*

*a dental cleaning member detachably attached to the handle, the dental cleaning member having a material composition, size, shape and mass defining a natural resonance frequency in resonance with the frequencies in the sonic range for allowing the vibrational energy produced by the counterweight to induce a resonance action in the dental cleaning member for reciprocating the dental cleaning member in a plane.*

*21. The device of claim 20, wherein said dental cleaning member comprises a toothbrush member.*

*22. The device of claim 20, wherein said dental cleaning member comprises a dental mouth tray member.*

*23. The device of claim 20, wherein said dental cleaning member comprises a toothpick member.*

*24. A device for cleaning teeth, comprising:*

*a handle containing an eccentric counterweight attached to a motor for rotating the counterweight to produce sonic range vibrational energy between 8,000 and 20,000 cpm, and*

*a dental cleaning member coupled to the handle, the dental cleaning member having a configuration defining a natural resonance frequency in resonance with the sonic range vibrational energy such that the sonic vibrational energy induces a resonance action in the dental cleaning member for moving the dental cleaning member.*

*25. The device of claim 24, wherein the dental cleaning member comprises a toothbrush member.*

*26. The device of claim 24, wherein the dental cleaning member comprises a floss-holding member.*

*27. The device of claim 24, wherein the dental cleaning member is detachable from the handle.*

*28. A device for cleaning teeth, comprising:*

*a handle containing an eccentric counterweight attached to a motor for rotating the counterweight to produce sonic range vibrational energy between 8,000 and 20,000 cmp, and*

*a dental cleaning member coupled to the handle, the dental cleaning member having a material composition, size, shape and mass defining a natural resonance frequency tuned to the sonic range vibrational energy such that the sonic range vibrational energy induces a resonance action in the dental cleaning member for reciprocating the dental cleaning member in a plane.*

*29. The device of claim 28, wherein the dental cleaning member comprises a toothbrush member.*

*30. The device of claim 28, wherein the dental cleaning member comprises a floss-holding member.*

*31. The device of claim 28, wherein the dental cleaning member is detachable from the handle.*

* * * * *